United States Patent [19]

Smirmaul

[11] 4,336,805
[45] Jun. 29, 1982

[54] CORNEAL TREPHINE

[76] Inventor: Heinz Smirmaul, 1207 Spring Lake Dr., Duncanville, Tex. 75137

[21] Appl. No.: 175,577

[22] Filed: Aug. 5, 1980

Related U.S. Application Data

[63] Continuation of Ser. No. 17,492, Mar. 5, 1979, abandoned.

[51] Int. Cl.³ .............................................. A61B 17/32
[52] U.S. Cl. .................................... 128/310; 128/305
[58] Field of Search .................. 128/310, 305.1, 305, 128/751–755; 408/703

[56] References Cited

U.S. PATENT DOCUMENTS 4,078,555  3/1978  Takahashi ........................ 128/6 X

FOREIGN PATENT DOCUMENTS 2741663  3/1978  Fed. Rep. of Germany ...... 128/305

OTHER PUBLICATIONS

Donaldson et al. "A New Corneal Trephine" Trans. Ophthal. Soc. U.K. (1978) pp. 14–15.
Draeger, J. "Ein Halbautomatisches Elekrisches Keratom Fuer Die Lamellaere Keratoplastik" Klin. Mbl. Augenheilk 167 (1975).
Gradle "New Scleral Trephine" Jour. Am. Med. Assoc., vol. LX No. 19, (May 10,1913) p. 2045.
Gebruder Martin: Motor Trephine Promotional Literature (5/1977).
Drews "Corneal Trephine" Trans. Am Acad. Opthalmol. Otolaryngol. 78:223 (1974).
Kadesky "An Electric Automatic Trephine" Am. J. Opthalmol. 34:1038 (1951).
Lieberman "A New Corneal Trephine" Am. J. Opthalmol. 81:684 (1976).
Crock et al. "A New System of Microsurgery . . ." Br. J. Ophthalmol. 62:74 (1978).
Hans Geuder, Micro—Keraton Promotional Brochure.

*Primary Examiner*—Michael H. Thaler
*Attorney, Agent, or Firm*—Richards, Harris & Medlock

[57] ABSTRACT

The present invention relates to trephines and in particular to trephines used in corneal grafting.

1 Claim, 3 Drawing Figures

CORNEAL TREPHINE

This is a continuation of application Ser. No. 17,492 filed Mar. 5, 1979, now abandoned.

BACKGROUND OF THE INVENTION

In some types of corrective surgery for eyes it becomes necessary to transplant corneal tissue from a donor to a recipient. In performing this transplant operation a corneal trephine is used. A corneal trephine is a surgical instrument used to cut a circular section or button from the corneal tissue. In performing the transplant operation a trephine is used to remove a button or cylindrical portion of transplant tissue from the donor's cornea and is used to form an opening in the recipient's cornea into which the transplant tissue is placed.

It is of critical importance to cut the opening in the recipient's eye as close as possible to the same size and shape as the button cut from the donor's eye. It has been found that the cornea is an elastic structure and that shear deformities can occur during the cutting process which distort the shape of the corneal button and cause discrepancies between the donor and recipient cuts.

In performing corneal grafting operations, an undistorted and unobstructed view of the cutting is important. Surgeons now use operating microscopes to view the graft to obtain a better view of the cutting steps.

Corneal trephines which are currently available either do not provide a full view of the cutting operation or tend to cause distortions in the cutting operation.

DISCLOSURE OF THE INVENTION

A corneal trephine is provided which allows full view of the cutting operation and tends to reduce distortion in the cutting operation. A ring shaped body is provided with a grasping surface. A ring shaped bevel gear is mounted for rotation in the body about an axis parallel to the axis of the body. A flexible drive cable is connected to the body to extend at an angle perpendicular to the axis of rotation of the bevel gear. The flexible drive cable is geared to drive the bevel gear. Thus the body of the trephine can be grasped by one hand of the surgeon while the other hand can manipulate the drive cable to rotate the gear. A cylindrical adapter preferably of transparent material is removably connected to the bevel gear. A disposable trephine assembly is removably connected to the cylindrical adapter at the end remote from the bevel gear. The disposable trephine assembly comprises a clear plastic circular disk with a cylindrical blade mounted in the center thereof whereby the cylindrical blade is rotated by the movement of the bevel gear and is clearly visible during use.

BRIEF DESCRIPTION OF THE DRAWINGS

For a more complete understanding of the present invention and the advantages thereof, reference is now made to the following description taken in conjunction with the accompanying drawings in which.

DETAILED DESCRIPTION OF THE INVENTION

Figure 1:
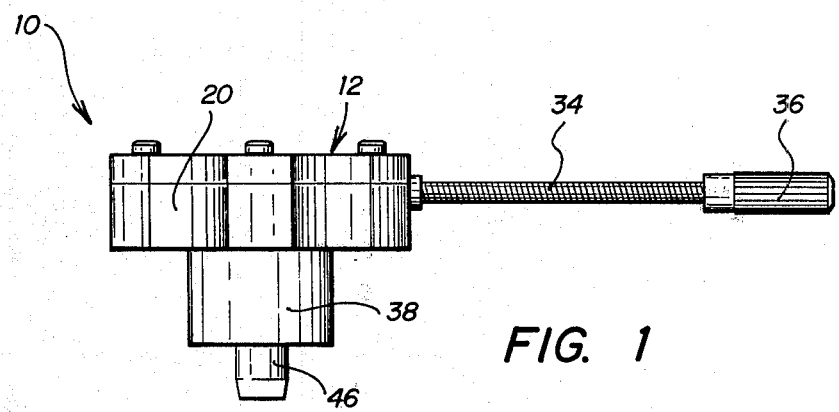
FIG. 1 is a side elevation view of the corneal trephine of the present invention.
Figure 2:
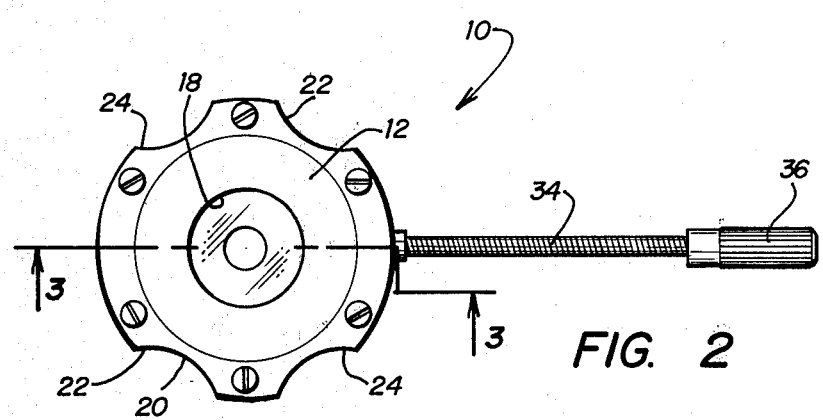
FIG. 2 is a top plan view of the trephine illustrated in FIG. 1.
Figure 3:
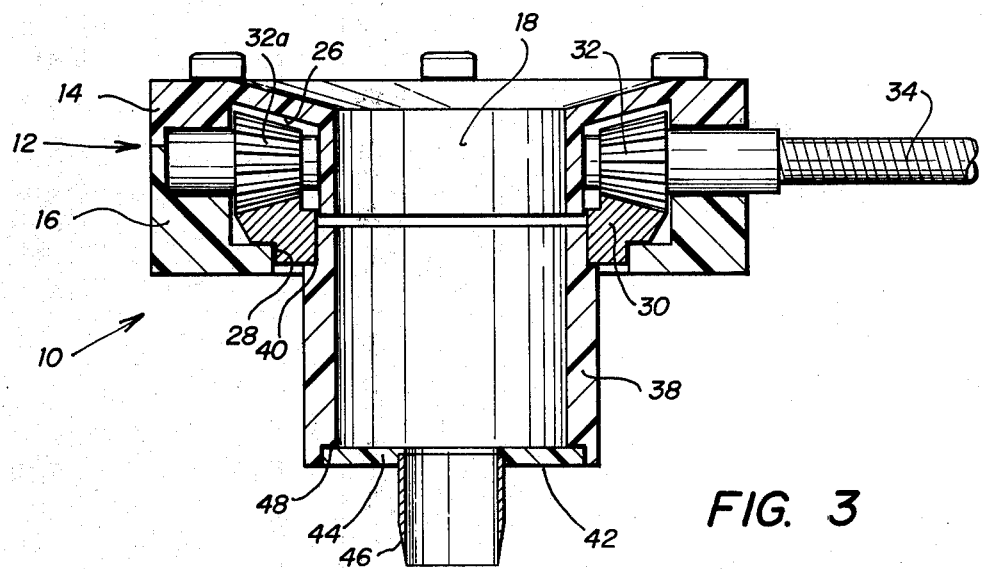
FIG. 3 is a sectional view taken along line 3—3 of FIG. 2 looking in the direction of the arrows.

A preferred embodiment of the apparatus of the present invention is shown in FIGS. 1 through 3. In these figures like reference numerals are utilized to designate like parts.

For purposes of description the corneal trephine assembly is designated as reference numeral 10. Assembly 10 is used by a surgeon to perform a corneal transplant and is specifically utilized to remove a cylindrical or button shaped portion of the cornea from a donor's eye and to form an opening in the recipient's eye.

The assembly 10 has a ring shaped body 12. In the present embodiment, the body 12 is formed from upper and lower sections 14 and 16 (FIG. 3) which are releasably connected together by suitable fasteners. The interior wall of the body 12 has a central opening 18.

The peripheral wall of the body 12 defines a grasping surface. As can be seen in FIG. 2, this grasping surface is provided with two pairs of opposing arcuate portions 22 and 24. These sets 22 and 24 allow the base to be grasped by the index finger and thumb of either the right or left hand during surgery. In the present embodiment, the body 12 is generally symmetrical about its axis so that it is balanced and easier to handle.

An annular chamber 26 is formed between upper and lower sections 14 and 16. This chamber 26 has suitable bearing surfaces 28 formed therein for receiving a ring gear 30 for rotation therein. A drive pinion gear 32 is rotatably mounted within the body 12 and is positioned to mesh with the ring gear 30. Gear 32 can be utilized to selectively drive the ring gear 30 in either a clockwise or counterclockwise direction. The gear ratio between ring gear 30 and the pinion 32 is preferably selected to be a 4 to 1 ratio. It is to be understood that other gear ratios could be utilized as preferred by the individual surgeon. Alternatively, more than one additional idler pinion (32a) can be provided within the body to add stability to the ring gear 30.

A flexible drive shaft 34 of a suitable length is connected to the pinion gear 32. A drive handle 36 is formed on the end of the flexible drive shaft. Handle 36 can be grasped by the surgeon and utilized to rotate drive shaft 34 which is in turn connected to gear 32 which drives ring gear 30. Thus, the handle 36 can be manipulated to selectively rotate ring gear 30.

An adapter 38 is releasably connected to the ring gear 30. In the embodiment shown, the adapter 38 is cylindrical in shape and has an angular groove 40 for frictional attachment to the protruding end of the ring gear 30. It is to be understood, of course, that other suitable means could be used to attach the adapter 38 to the gear 30. According to a particular feature of the present invention, the cylindrical adapter 38 is formed from a transparent material to provide a full view of the surgical operation through the central opening 18.

Releasably attached to the adapter 38 is a disposable trephine assembly 42. Trephine assembly 42 comprises a transparent disk 44 and a cylindrical blade 46. Blade 46 is positioned in the center of the clear plastic disk 44 and a second annular groove 48 is formed in the adapter 38 for frictionally engaging the clear plastic disk 44 in the position shown in FIG. 3. In the embodiment shown, the trephine assembly 42 is frictionally attached to the adapter 38, but it is to be understood, of course, that other attachment means could be used.

According to a particular feature of the present invention, the adapter 38 and the disk 44 of trephine assembly 42 are transparent to provide an unobstructed and undistorted view of the cutting operation by the surgeon.

In use, the body 12 is grasped in one hand by the surgeon. This allows the surgeon to steady that hand on the forehead of the patient to give the surgeon full control over the position of the blade 46 during the cutting operation. By providing the body portion 12 with the arcuate portions 22 and 24 thereon, the surgeon can grasp the body 12 with the index finger and thumb and steady the assembly 10 by resting a portion of his hand on the forehead of the patient. This ensures full control over the position of the blade 46 and allows the surgeon to properly move the blade 46 without distorting the corneal button.

In addition, flexible shaft 34 can, for example, be approximately 6 inches long. This allows the surgeon to utilize the other hand to rotate the blade 46 through shaft 34 without disturbing the hand providing position control of the body 12. The flexible shaft 34 isolates movement of the two hands of the surgeon. Thus, unnecessary or uncontrolled movements in the hand providing the driving force through shaft 34 are isolated from the body 12 stabilized by the other hand. In addition, the rotational driving movement is provided about an axis extending transverse to the axis the cylindrical cutter thus further improving the stability of the trephine during use.

By providing a gearing drive arrangement, various gear ratios can be selected between the pinion 32 and ring 30 gears to allow the knife blade 46 to be rotated as fast or as slow as desired.

By providing the trephine assembly 10 with an adapter 38 which is removably attached to the ring gear 40, the adapter 38 can be removed and sterilized or disposed of as required. In addition, adapters of various sizes and lengths can be utilized with the base to accommodate various problems presented by the operation to be performed.

The provision for a removable trephine assembly 42 allows the use of disposable trephine assemblies. This allows the use of a fresh cutting blade for each operation to ensure sharp and sterile operation. The removable assembly 42 allows the use of various diameter blades 46 to remove corneal buttons of different sizes.

The transparent plastic disk 44 and adapter 38 enhance the surgeon's view of the operation by removing the body of the apparatus further away from the eye and allowing light under the apparatus to provide a clear view through the center of the assembly 10.

Thus the present invention provides a corneal trephine which is easier to stabilize during surgery by isolating the driving or rotating force through a flexible drive shaft. In addition, a clear view of the operation is also provided.

Although a particular embodiment of the present invention has been illustrated in the accompanying drawings and described in the foregoing detailed description, it is to be understood that the present invention is not to be limited to just the embodiment disclosed, but that it is capable of numerous rearrangements, modifications and substitutions without departing from the scope of the invention.

I claim:

1. A corneal trephine comprising: a ring shaped body having a central opening therethrough of a diameter greater than the diameter of the cornea;
   said ring shaped body having a chamber therein;
   a ring gear mounted within said chamber of said ring shaped body for rotation about an axis extending through said ring shaped body;
   cylindrical adapter means of transparent material and having first and second ends and being aligned with said central opening of said ring shaped body;
   said cylindrical adapter means being releasably coupled at said first end to said ring gear for rotation about said axis;
   said cylindrical adapter means having an opening therethrough of diameter greater than the diameter of the cornea;
   said second end of said cylindrical adapter means including an annular groove;
   transparent disk means having a diameter greater than the diameter of the cornea and being releasably received by said annular groove in said second end of said cylindrical adapter means to facilitate removal and disposal of said transparent disk means;
   cylindrical cutting blade means for axially cutting the cornea and having a selectable predetermined diameter less than the diameter of said transparent disk means and being mounted concentrically on said transparent disk means;
   flexible drive shaft means extending from said ring shaped body and transversely disposed to said axis;
   means for connecting said flexible drive shaft means to said ring gear for rotating said cylindrical adapter means and said cylindrical cutting blade means about said axis; and
   said connecting means including bearing means mounted within said chamber for supporting said ring gear and pinion gear means connected to said flexible drive shaft means and being rotatably mounted within said chamber for meshing with said ring gear.

* * * * *